United States Patent
Fyles

(10) Patent No.: US 8,076,390 B2
(45) Date of Patent: Dec. 13, 2011

(54) ANTIFOULING POLYMERIC AGENT FOR MARINE APPLICATIONS

(75) Inventor: Thomas M. Fyles, Victoria (CA)

(73) Assignee: UVIC Industry Partnerships Inc., Victoria, B.C. (CA)

( * ) Notice: Subject to any disclaimer, the term of this patent is extended or adjusted under 35 U.S.C. 154(b) by 657 days.

(21) Appl. No.: 11/564,781

(22) Filed: Nov. 29, 2006

(65) Prior Publication Data

US 2007/0129461 A1    Jun. 7, 2007

Related U.S. Application Data

(60) Provisional application No. 60/741,785, filed on Dec. 1, 2005.

(51) Int. Cl.
- *C08K 5/34* (2006.01)
- *C09D 5/16* (2006.01)
- *A01N 35/00* (2006.01)
- *C08G 73/00* (2006.01)
- *C08G 73/06* (2006.01)

(52) U.S. Cl. .......... 523/122; 524/99; 524/100; 524/102; 514/579; 514/634; 528/363; 528/422; 528/423; 525/917

(58) Field of Classification Search .................. 523/122; 524/99, 100, 102; 514/579, 634; 528/363, 528/422, 423; 525/917
See application file for complete search history.

(56) References Cited

U.S. PATENT DOCUMENTS

| | | | | |
|---|---|---|---|---|
| 5,126,374 A | * | 6/1992 | Zipplies et al. | 514/634 |
| 6,518,309 B1 | * | 2/2003 | Fyles et al. | 514/579 |
| 2002/0177627 A1 | | 11/2002 | Fyles et al. | |
| 2005/0080159 A1 | * | 4/2005 | Omoto et al. | 523/122 |

FOREIGN PATENT DOCUMENTS

| | | |
|---|---|---|
| DE | 21 44 125 | 3/1973 |
| GB | 1 091 049 | 11/1967 |
| JP | 01-129077 | 5/1989 |
| JP | 03-252462 | 11/1991 |
| WO | WO 01/79359 | 10/2001 |

OTHER PUBLICATIONS

International Search Report, issued Oct. 23, 2001, by the European Patent Office, for International Patent Application No. PCT/CA 01/00112.

Jacobson, A.H. et al., "Sea-Nine Antifoulant: An Environmentally Acceptable Alternative to Organotin Antifoulants," *Science of the Total Environment*, vol. 258, pp. 100-103 (2000).

Omae, I., Organotin Antifouling Paints and Their Alternatives, *Applied Organometallic Chemistry*, vol. 17, pp. 81-105 (2003).

* cited by examiner

*Primary Examiner* — Kriellion Sanders

(74) *Attorney, Agent, or Firm* — Klarquist Sparkman, LLP

(57) ABSTRACT

The present invention provides a composition for use as an antifouling agent and a method of decreasing fouling of a surface in a marine environment. The composition is a polymeric matrix, the polymeric matrix comprising subunits of at least one structural monomer and at least one ionic monomer. The ionic monomer comprising a salt, that is an anion that is a conjugate base of an acid having a $pK_a$ less than about 9 and at least one cation that is a cationic biocide. One embodiment includes guanidinium counterions that undergo ion exchange to slowly release a biocidal component.

40 Claims, No Drawings

ANTIFOULING POLYMERIC AGENT FOR MARINE APPLICATIONS

CROSS REFERENCE TO RELATED APPLICATION

This application claims the benefit of the earlier filing date of U.S. patent application Ser. No. 60/741,785, entitled Antifouling Polymeric Agent for Marine Applications, which was filed on Dec. 1, 2005, and is incorporated herein by reference.

FIELD

The invention relates to antifouling agents for aquatic environments. More specifically, the invention relates to guanidinium counterions that undergo ion exchange to slowly release a biocidal component.

BACKGROUND

Underwater surfaces are subject to fouling by a complex fouling community involving many different organisms. The primary fouling organisms include bacteria, diatoms, and algal spores. Bacteria are the first organisms to attach and likely lay down a conditioning film on the surface. Their attachment is followed by that of diatoms and algal spores. Hard fouling organisms appear in the second stage of fouling and include barnacles, algae, mollusks, tube worms, and sponges.

Tributyltin (TBT) and organotin derivatives like tributyltin oxide (TBTO) have been the most effective antifouling biocides in use to date. However, their use has many severe environmental consequences. These antifoulants are highly toxic to non-target aquatic organisms, they bioaccumulate with accumulation factors as high as 10,000, their degradation products are highly toxic, and they are believed to be endocrine disruptors.

Since the application of organotins was banned in 2003 the search for alternatives has begun. Copper oxide is the commonly used alternative at present, but since it is not very effective against algae and diatoms, it is usually used in conjunction with an organic booster biocide to help control these organisms. (Omae, I. "Organotin antifouling paints and their alternatives" *Applied Organometallic Chemistry* 2003, 17, 81-105.)

Based on the impact of TBT and its derivatives on the near-shore marine environment, the environmental fate of new marine antifouling biocides is subject to regulatory scrutiny. This poses a key dilemma for the invention of new antifouling coatings. On the one hand, the active agents must degrade to non-toxic byproducts at a sufficiently rapid rate that prevents their accumulation in the environment. On the other hand, an effective antifouling coating must have a long effective lifetime in contact with seawater. A currently used antifoulant Sea-Nine™ (4,5-dichloro-2-octyl-4-isothiazolin-3-one) meets the former criterion, rapidly degrading via ring opening reactions. However, Sea-Nine is simply dispersed in a suitable support matrix such as paint and leaches into the environment at a rate that depends upon diffusion through the supporting matrix. A constant effective concentration is therefore difficult to sustain over a prolonged period. (Jacobson, A. H.; Willingham, G. L. "Sea-nine antifoulant: an environmentally acceptable alternative to organotin antifoulants" *Science of the Total Environment* 2000, 258, 103-100.)

Research on poly-substituted guanidinium salts has shown that they are able to inhibit growth of algal communities. In laboratory experiments, the exposed algal communities recover and grow once the active agent has degraded to a low concentration. However, in order to use the salts as antifouling agents, they have to be formulated in mixtures that can be used to coat the surface to be protected. Attempts to employ the mixtures in the field demonstrated that the effective lifetime of the mixtures was limited, with the lifetime dependent upon the temperature of the marine environment. (Fyles, T. M.; Rowe, R. D. "Microbiocidal properties of poly-substituted guanidinium salts" U.S. Pat. No. 6,518,309 B1 2003).

Known slow-release marine coating formulations employ a wide variety of strategies. The principal strategy exploits the physical ablation of the surface by motion of water past the treated surface, so-called "self-polishing" surfaces. This continually exposes fresh surface, either for diffusive release of a soluble component such as Sea-Nine, or the exposure of an insoluble component such as copper oxide. Such a strategy requires significant water movement and is ineffective on slow moving or fixed submarine structures. An alternative strategy relies on a chemical reaction with the seawater to release a continuous supply of the active agent which is initially attached to the coating matrix. This was particularly effective for esters of TBT which hydrolyzed at acceptable rates to release tributyltin oxide. (Omae, op cit.) Such hydrolysis reactions can be used in conjunction with the self-polishing strategy to release insoluble materials such as copper oxide, but are not appropriate for biocides such as Sea-Nine which readily diffuse through the matrix, and themselves undergo hydrolysis reactions at appreciable rates. Release of ionic components such as copper, zinc, or alkylammonium salts via acid-base reactions with a supporting matrix has also been described. Such processes are subject to the particular chemical properties of the ions released and do not offer a general method. (Iwamura, G.; Konno, E.; Shoji, A.; Yokoyama, Y.; Tatsuno, Y.; Shimizu, S. "Antifouling coatings containing difficultly hydrolysable acrylic polymers, Japanese patent JP01129077 A2 1989; Arimoto, Y.; Hayashi, S.; Rakutani, K; Shoida, Y. "Durable marine antifouling paints", Japanese patent JP 03252462 A2 1991).

There is therefore a need for antifouling formulations containing environmentally acceptable agents that can be formulated to slowly release an effective concentration of the active agent. It is an object of the present invention to overcome the deficiencies in the prior art.

SUMMARY

The present invention provides a composition for use as an antifouling agent, the composition being a polymeric matrix, the polymeric matrix comprising:

subunits of at least one structural monomer; and at least one ionic monomer, the ionic monomer comprising a salt, the salt comprising an anion that is a conjugate base of an acid having a $pK_a$ less than about 9 and at least one cation that is a cationic biocide.

In one aspect of the invention, the polymeric matrix comprises about 20-70 wt % ionic monomer.

In another aspect of the invention, the polymeric matrix comprises about 20-40 wt % ionic monomer.

In another aspect of the invention, the polymeric matrix comprises about 30 wt % ionic monomer.

In another aspect of the invention, the polymeric matrix comprises at least two structural monomers.

In another aspect of the invention, the cationic biocide is selected from the group consisting of guanidinium cations of general formula:

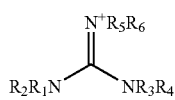

wherein $R_1$, $R_2$, $R_3$, $R4$, $R_5$ and $R_6$ is selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R_4$, $R_5$ and $R_6$ are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, quaternary ammonium cations of general formula:

$R_1R_2R_3R_4N^+$ where $R_1$, $R_2$, $R_3$, and $R_4$ are independently selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and pyridinium cations comprising:

N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2,3,4, or 5-substituted pyridinium compounds where the N substituent is selected from alkyl, branched alkyl, substituted alkyl, alkenyl, aryl or heteroaryl and where the 2, 3, 4 or 5-substituents are independently selected from the group alkyl, branched alkyl, substituted alkyl, alkenyl, aryl, heteroaryl, hydroxyl, O-alkyl, O-aryl, cyano, nitro, chloro, bromo, formyl, or acetyl.

In another aspect of the invention, the ionic monomer comprises polysubstituted guanidinium methacrylate.

In another aspect of the invention, the cationic biocide is N-butyl-N'decylguanidinium or N-butyl-N'decyl-N"-(3-hydroxylpropyl)guanidinium.

In another aspect of the invention, the structural monomers are selected from alkyl, branched alkyl, or aryl esters of acrylic acid, substituted acrylic acids such as methacrylic acid, or other alkyl, polyalkyl, or substituted alkyl acrylic acids; esters of acrylic acid, substituted acrylic acids such as methacrylic acid, or other alkyl, polyalkyl, or substituted alkyl acrylic acids with diols, triols, or other polyols; alkyl, substituted alkyl, branched alkyl, or aryl amides of acrylic acid, substituted acrylic acids such as methacrylic acid, or other alkyl, polyalkyl, or substituted alkyl acrylic acids; amides of acrylic acid, substituted acrylic acids such as methacrylic acid, or other alkyl, polyalkyl, or substituted alkyl acrylic acids with dimaines, triamines or other polyamines; styrene; substituted styrenes; acrylonitrile, substituted acrylonitriles, vinyl acetate or other vinyl esters of alkanoic, substituted alkanoic, benzoic, or substituted benzoic acids; vinyl chloride; alkenes, dienes, other polyvinylic or polyalkenyl compounds.

In another aspect of the invention, the structural monomers comprise 2-ethylhexyl acrylate, and methyl methacrylate.

In another aspect of the invention, 2-ethylhexyl acrylate comprises about 20-30 wt %, and methyl methacrylate comprises about 20-40 wt % of the composition.

In another embodiment of the invention, a composition for use as an antifouling agent is provided. The composition is synthesized from subunits of at least one structural monomer; and at least one ionic monomer, the ionic monomer comprising a salt, the salt comprising an anion that is a conjugate base of an acid having a $pK_a$ less than about 9 and at least one cation that is a cationic biocide.

In one aspect of the invention, the polymeric matrix is synthesized from about 20-70 wt % ionic monomer.

In another aspect of the invention, the polymeric matrix is synthesized from about 20-40 wt % ionic monomer.

In another aspect of the invention, the polymeric matrix is synthesized from about 30 wt % ionic monomer.

In another aspect of the invention, the polymeric matrix is synthesized from at least two structural monomers.

In another aspect of the invention, the cationic biocide for synthesis of the polymeric matrix is selected from the group consisting of guanidinium cations of general formula:

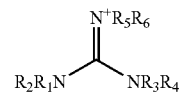

wherein $R_1$, $R_2$, $R_3$, $R_4$, $R_5$ and $R_6$ is selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R4$, $R_5$ and $R_6$ are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, quaternary ammonium cations of general formula:

$R_1R_2R_3R_4N^+$ where $R_1$, $R_2$, $R_3$, and $R_4$ are independently selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and pyridinium cations comprising:

N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2,3,4, or 5-substituted pyridinium compounds where the N substituent is selected from alkyl, branched alkyl, substituted alkyl, alkenyl, aryl or heteroaryl and where the 2, 3, 4 or 5-substituents are independently selected from the group alkyl, branched alkyl, substituted alkyl, alkenyl, aryl, heteroaryl, hydroxyl, O-alkyl, O-aryl, cyano, nitro, chloro, bromo, formyl, or acetyl.

In another aspect of the invention, the cationic biocide for synthesis of the polymeric matrix is selected from the group consisting of guanidinium cations of the general formula:

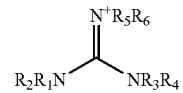

wherein $R_1$, $R_2$, $R_3$, $R_4$, $R_5$ and $R_6$ is selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R_4$, $R_5$ and $R_6$ are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

In another aspect of the invention, the ionic monomer for synthesis of the polymeric matrix comprises polysubstituted guanidinium methacrylate.

In another aspect of the invention, the cationic biocide for synthesis of the polymeric matrix is N-butyl-N'decylguanidinium or N-butyl-N'decyl-N''-(3-hydroxylpropyl) guanidinium.

In another aspect of the invention, the structural monomers for synthesis of the polymeric matrix are selected from alkyl, branched alkyl, or aryl esters of acrylic acid, substituted acrylic acids such as methacrylic acid, or other alkyl, polyalkyl, or substituted alkyl acrylic acids; esters of acrylic acid, substituted acrylic acids such as methacrylic acid, or other alkyl, polyalkyl, or substituted alkyl acrylic acids with diols, triols, or other polyols; alkyl, substituted alkyl, branched alkyl, or aryl amides of acrylic acid, substituted acrylic acids such as methacrylic acid, or other alkyl, polyalkyl, or substituted alkyl acrylic acids; amides of acrylic acid, substituted acrylic acids such as methacrylic acid, or other alkyl, polyalkyl, or substituted alkyl acrylic acids with dimaines, triamines or other polyamines; styrene; substituted styrenes; acrylonitrile, substituted acrylonitriles, vinyl acetate or other vinyl esters of alkanoic, substituted alkanoic, benzoic, or substituted benzoic acids; vinyl chloride; alkenes, dienes, other polyvinylic or polyalkenyl compounds.

In another aspect of the invention, the polymeric matrix is synthesized from structural monomers comprising 2-ethylhexyl acrylate, and methyl methacrylate.

In another aspect of the invention, the polymeric matrix is synthesized from methacrylate salt of (N-butyl-N'decyl-N''-(3-hydroxylpropyl)guanidinium chloride), methyl methacylate and 2-ethylhexylacrylate.

In another embodiment of the invention, a method of decreasing fouling of a surface in a marine environment is provided. The method comprises treating said surface with an antifouling agent comprising a polymeric matrix comprising:
    subunits of at least one structural monomer; and
    at least one ionic monomer, the ionic monomer comprising a salt, the salt comprising an anion that is a conjugate base of an acid having a $pK_a$ less than about 9 and at least one cation that is a cationic biocide.

In one aspect of the method of the invention, the surface is treated with the polymeric matrix comprising about 20-30% 2-ethylhexyl acrylate and about 20-40 wt % methyl methacrylate.

In another aspect of the method of the invention, the surface is treated with a composition synthesized from methacrylate salt of (N-butyl-N'decyl-N''-(3-hydroxylpropyl) guanidinium chloride), methyl methacylate and 2-ethylhexylacrylate.

In yet another aspect of the invention, treating comprises coating.

Structural Monomers:

Structural monomers include monomers that can impart mechanical strength to a polymer, impart hydrophobicity to the coating, enhance processibility of the polymer, or any useful combination of mechanical strength, hydrophobicity, and processibility. These include substituted alkyl, branched alkyl, or aryl esters of acrylic acid, substituted acrylic acids such as methacrylic acid, or other alkyl, polyalkyl, or substituted alkyl acrylic acids; esters of acrylic acid, substituted acrylic acids such as methacrylic acid, or other alkyl, polyalkyl, or substituted alkyl acrylic acids with diols, triols, or other polyols; alkyl, substituted alkyl, branched alkyl, or aryl amides of acrylic acid, substituted acrylic acids such as methacrylic acid, or other alkyl, polyalkyl, or substituted alkyl acrylic acids; amides of acrylic acid, substituted acrylic acids such as methacrylic acid, or other alkyl, polyalkyl, or substituted alkyl acrylic acids with dimaines, triamines or other polyamines; styrene; substituted styrenes; acrylonitrile, substituted acrylonitriles, vinyl acetate or other vinyl esters of alkanoic, substituted alkanoic, benzoic, or substituted benzoic acids; vinyl chloride; alkenes, dienes, other polyvinylic or polyalkenyl compounds.

Guanidinium Cations:
Of general formula

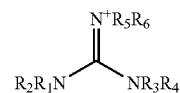

wherein $R_1$, $R_2$, $R_3$, $R_4$, $R_5$ and $R_6$ are independently selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R_4$, $R_5$ and $R_6$ are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

Quaternary Ammonium Cations:
Of general formula $R_1R_2R_3R_4N^+$ where $R_1$, $R_2$, $R_3$, and $R_4$ are independently selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

Pyridinium Cations:
N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2,3,4, or 5-substituted pyridinium compounds where the N substituent is selected from alkyl, branched alkyl, substituted alkyl, alkenyl, aryl or heteroaryl and where the 2, 3, 4 or 5-substituents are independently selected from the group alkyl, branched alkyl, substituted alkyl, alkenyl, aryl, heteroaryl, hydroxyl, O-alkyl, O-aryl, cyano, nitro, chloro, bromo, formyl, or acetyl. More specifically, N,N'-dimethyl-4,4'-bipyridinium and N-methyl-4-cyanopyridinium and even more specifically N,N'-dimethyl-4,4'-bipyridinium.

Anionic Monomers:
The conjugate base forms of: acrylic acid; substituted acrylic acids such as methacrylic acid; other alkyl, polyalkyl, or substituted alkyl acrylic acids; styrene carboxylic acid; other alkyl, polyalkyl, or substituted styrene carboxylic acids; styrenesulfonic acid; other alkyl, polyalkyl, or substituted styrene sulfonic acids.

Ionic Monomers:
A salt consisting of a guanidinium or quaternary ammonium or pyridinium cation and an anionic monomer.

Common Initiators of Radical Polymerization:
For thermally initiated, direct photolysis initiated, or sensitized photolysis initiated polymerization in organic solvents: peroxides of general formula $R_1$—O—O—$R_2$ where $R_1$ and $R_2$ are independently selected from the list of hydrogen, alkyl, substituted alkyl, aryl, substituted aryl, alkanoyl, substituted alkanoyl, benzoyl, and substituted benzoyl; azo compounds of general formula $R_1$—N═N—$R_2$ where $R_1$ and $R_2$ are independently selected from the list of alkyl, substituted alkyl, cyanoalkyl; diazo compounds of general formula $N_2$—R where R is alkyl, branched alkyl, alpha-keto alkyl, or alpha-ketoaryl.

For thermally initiated polymerizations in aqueous solvents: peroxides such as hydrogen peroxide; peracids such as peracetic, peralkanoic, or perbenzoic acids; persulfate salts such as ammonium persulfate; cerium(IV) salts such as cerium ammonium nitrate; manganese (III) salts such as manganese (III) nitrate; samarium salts such as samarium diiodide.

Subunits:

A subunit is a repeating unit of a polymer. The smallest subunit is a monomer. Dimers, trimers, tetramers and other oligomers, all of which implicitly contain monomers, are also subunits.

Polymeric Matrix:

A composition comprising subunits of at least one ionic monomer and subunits of at least one structural monomer, polymerized by a radical polymerization initiated by one or more common initiators of radical polymerization.

Percentages of Reactants for Synthesis:

The preferred percentages used for synthesis are as follows:

ionic monomer or total of more than one ionic monomer in a mixture—about 20-70 wt %, preferably about 20-40 wt %, more preferably about 30%; and structural monomer or total of more than one structural monomer in a mixture—about 80-30 wt %, preferably about 80-60 wt %, more preferably about 70 wt %.

Percentage of Products in Polymers:

The preferred percentages in the polymers are as follows:

ionic monomer or total of more than one ionic monomer in a mixture—about 20-70 wt %, preferably about 20-40 wt %, more preferably about 30 wt %; and structural monomer or total of more than one structural monomer in a mixture—about 80-30 wt %, preferably about 80-60 wt %, more preferably about 70 wt %.

Overview:

A composition consisting of a poly substituted guanidinium salt of an anionic polymer can be used as an antifouling agent. Surfaces can be treated with the composition by coating, impregnating, covering, dispersing, layering or similar methods, as would be known to one skilled in the art. The poly-substituted guanidinium cations have the general formula:

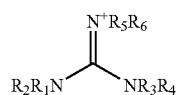

wherein $R_1$, $R_2$, $R_3$, $R_4$, $R_5$ and $R_6$ are independently selected from the group consisting of alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R_4$, $R_5$ and $R_6$ are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl. We have previously shown that the chloride salts of these poly-substituted guanidinium cations are active against both bacterial and algal microbiota, and at the same time inhibit the settling and growth of barnacles and they degrade at an acceptable rate in seawater to non-toxic components. While the chloride salts were effective biocides, as noted above, the lifetime of the mixtures containing the active ingredient was limited and hence there was a need to extend the lifetime of the active coating through a slow release strategy. Although the choices outlined above were possible, the ionic nature of the salts themselves allows for a new type of slow-release mechanism that involves an ion exchange reaction. With this new strategy, the active component, a cation, would be bound to the polymeric matrix, an anion, via an ionic interaction. No hydrolysis reaction would be required for release, and water alone would be insufficient to release the active component. Release would only occur in the presence of an exchanging cation from the seawater, via the ion exchange reaction:

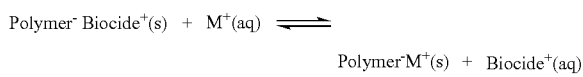

The species "Polymer⁻" is a polymer containing an anionic group such as a carboxylate, sulfonate, or phosphate. In order to form suitable protective coatings, "Polymer⁻" will contain structural components to impart mechanical strength and other desirable characteristics in addition to the ion exchange capability of the agent. The species $M^+$ is a cation such as sodium, potassium, calcium, magnesium, other alkaline metal and alkaline earth cations or combinations thereof. The species "biocide⁺" is a member of polysubstituted guanidinium salts of general formula shown above or other cationic biocides.

Based upon these considerations we targeted acrylate terpolymers consisting of an alkylacrylate (2-ethylhexyl methacrylate) as a hydrophobic component to produce tough coatings, methyl methacrylate as a component to provide mechanical strength, and the methacrylate salts of the guanidinium cation as the ion exchange component. The methacrylate salts were prepared from chloride salts via ion exchange. Since these salts are freely soluble in organic solvents, we were able to polymerize a mixture of components using either radical initiated polymerization in xylene solution, or radical initiated emulsion polymerization in water. The resultant polymers were cast on test panels and deployed in the ocean to establish the effectiveness of the antifouling activity.

Although we specifically investigated the properties of coatings containing poly-substituted guanidinium salts as the active biocidal component, it will be obvious that other cationic biocides such as cationic surfactants bearing a quaternary ammonium groups or N-substituted pyridinium cations would be amenable to a similar formulation. The bactericidal activity of chloride and bromide salts of these cations is well known, and the marine antifouling activity of such salts has been reported by others. (Smith, M. J.; Adma, G.; Duncan, H. J.; Cowling, M. J. "The effects of cationic surfactants on marine biofilm growth on hydrogels" *Estuarine, Coastal, and Shelf Science* 2002, 55, 361-367.)

EXAMPLES

Example 1

Slow release formulation containing N-butyl-N'decylguanidinium prepared by emulsion polymerization This example describes the preparation of the methacrylate salt of N-butyl-N'decylguanidinium via an ion exchange method, and the formation of a ter-polymer from this monomer plus methyl methacylate and 2-ethylhexylmethacrylate as the other co-monomers using a radical initiated emulsion polymerization reaction. Coatings prepared from the product polymer were assessed for marine antifouling activity in two field experiments.

Amberlite® IRA-400 (Cl) ion exchange resin (100 g) was washed successively with 2.0 M aqueous sodium hydroxide (1 L), methanol (1 L), 0.9 M methacrylic acid in methanol (1 L), and methanol (0.5 L). This resin was then washed with a solution of N-butyl-N'decylguanidinium chloride (35 g; prepared as previously described) in methanol (500 mL) followed by a further 500 mL portion of methanol. The combined methanol washings were evaporated and stored at −4° C. until used in a subsequent step. The product N-butyl-N'decylguanidinium methacrylate gave the following NMR data:

$^1$H NMR (CDCl$_3$, ppm): δ7.44 and 6.9 (br s, 4H total), 5.72 (d, 2.2 Hz, 1H), 5.17 (m, 1H), 3.27-3.14 (m, 4H), 1.85 (s, 3H), 1.49-1.65 (m, 4H), 1.45-1.15 (m, 14H), 0.93-0.78 (m, 8H).

Sodium dodecyl sulfate (0.05 g) and ammonium persulfate (0.1 g) were dissolved in water (9.9 mL) and heated to 85° C. To this solution were added dropwise a mixture of methyl methacrylate (2.7 mL) and 2-ethylhexyl methacrylate (5.7 mL) from one dropping funnel, and simultaneously N-butyl-N'decylguanidinium methacrylate (2.5 g) from a second dropping funnel (wt % monomers: methyl methacrylate 23 wt %, 2-ethylhexylmethacrylate 56 wt %, N-butyl-N'decylguanidinium methacrylate, 22 wt %). After an initial addition of approximately 10% of each of the monomers, the mixture was stirred at 85° C. until it was persistently milky. The remaining monomers were then added dropwise over a period of two hours followed by a period of stirring at 95° C. for a further one hour. At this point the reaction mixture was grainy. After cooling to 85° C., a further amount of the initiator ammonium persulfate (0.5 g) was added in a single portion. This produced a single mass of polymer within a few minutes, and the reaction mixture was cooled and the polymer was recovered by decanting the supernatant. Elemental analysis of the product for N gave 3.2 wt % N corresponding to a composition of 24 wt % N-butyl-N'decylguanidinium in the product.

Test panels were prepared from the polymer by evaporation of a xylene solution of the product polymer onto a 10×10 cm Plexiglass panel at a total loading of 0.01 g/cm$^2$. Replicate panels, together with controls prepared by a directly analogous method starting with tetrabuylammonium methacrylate, were mounted on test panels and submerged to a depth of 1 m in seawater. The test panels were occasionally raised to the surface for photography and assessment of the progress of marine fouling by algae, other biota, and barnacles.

Two experiments were conducted. The first involved a 32 day exposure in seawater with an average temperature of 28° C. Under these conditions, barnacles rapidly colonized the control panels (average 90±15 settled per panel after 22 days). Panels treated with the ter-polymer containing N-butyl-N'decylguanidinium were significantly less fouled (average 28±15 settled per panel after 22 days) than the corresponding control panels. In addition, many of the settled barnacles on the treated panel were small and some died after an initial growth. The initial barnacle fouling was followed by a slime of algae and microbiota. The slime thickness was scored on a 4 point scale from 0—"no slime", to 4—"very thick slime". After 32 days exposure, the control panels supported a "thick" to "very thick" slime layer (average score 3.2±1) while the panels treated with the ter polymer containing N-butyl-N'decylguanidinium supported only a "thin" slime layer (average score 1.2±0.8). Panels prepared as previously from a urethane paint with 10 wt % of N-butyl-N'decylguanidinium chloride dissolved in the matrix supported both barnacle settlement and algal growth that was statistically indistinguishable from untreated controls at both the 22 and 32 day analysis dates. Thus the biocidal activity of the N-butyl-N'decylguanidinium cation has been prolonged by the polymer formulation.

The second experiment was conducted in over a 4.5 month period in cool seawater with a temperature ranging from 11 to 14° C. over the course of the experiment. At this location the initial fouling of untreated controls was by brown algae and other microbiota, followed by abundant green algae within a few weeks. Barnacles were apparent after 3 months, and grew rapidly to cover untreated surfaces in the following 4-6 week period. Initial algal growth was scored on a 5 point scale from 0—"no algae" to 4—"surface completely covered in algae". After 42 days exposure, the control panels were substantially covered in algae (average score 3.2±0.5) while the panels containing N-butyl-N'decylguanidinium were significantly less covered by algae (average score 1.8±0.5). After 153 days the control panels had heavy fouling by barnacles (average 88±33 settled per panel). Panels containing N-butyl-N'decylguanidinium had significantly fewer settled barnacles (average 9±3 settled per panel) and some of these had died following initial growth. Panels prepared as previously from a urethane paint with 5 wt % of N-butyl-N'decylguanidinium chloride dissolved in the matrix supported both barnacle settlement and algal growth that was statistically indistinguishable from untreated controls at the 42 and 153 day analysis dates. Thus the biocidal activity of the N-butyl-N'decylguanidinium cation was been prolonged by the polymer formulation.

Example 2

Slow release formulation containing N-butyl-N'decyl-N"-(3-hydroxypropyl) guanidinium prepared by solution polymerization. This example describes the preparation of a new example of the previously reported class of biocidal guanidinium salts from N-buytl-N'decyl-iso-thiouronium chloride and 3-hydroxylpropyl amine. The methacrylate salt of the product (N-butyl-N'decyl-N"-(3-hydroxylpropyl)guanidinium chloride) was prepared via an ion exchange method, and a ter-polymer was finally prepared from this monomer plus methyl methacylate and 2-ethylhexylacrylate as the other co-monomers using a radical initiated solution polymerization reaction. Coatings prepared from the product polymer were assessed for marine antifouling activity in two field experiments.

N-Butyl-N'decyl-N"-methyl-iso-thiouronium chloride (10 g, 31 mmol) was dissolved in ethanol (50 mL) and 3-hyrdoxylpropyl amine (11.6 g, 155 mmol) was added. The mixture was stirred vigorously at reflux for 24 hours (CAUTION: methyl mercapatan is evolved. Use a fume hood). The solvent was removed by rotary evaporation and the product oil was dissolved in chloroform (100 mL). The chloroform was extracted with HCl (1M, 200 mL), dried (MgSO$_4$) and concentrated to give N-butyl-N'decyl-N"-(3-hydroxylpropyl)guanidinium chloride as a colorless viscous liquid. $^1$H NMR (CDCl$_3$, ppm): δ 8.26 (br s, 1H), 756-7.48 (br, 1H), 6.98-6.84 (br 1H). 3.63 (t, J=5.1 Hz, 2H), 3.38-3.49 (m, 2H), 3.31-3.19 (m, 4H), 1.69-1.82 (m, 2H), 1.62-1.489(m, 4H), 1.38-1.10 (m, 14H), 0.90-0.76 (m, 9H).

As described in example 1, the chloride anion was exchanged for a methacrylate anion by ion exchange to produce N-butyl-N'decyl-N"-(3-hydroxylpropyl)guanidinium methacrylate having the NMR spectral parameters of the staring material plus additional resonances for the methacrylate anion (δ5.77 (br, 1H), 5.22 (br, 1H), 1.82 (s, 3H).

The inhibitor hydroxyanisole was removed from methyl methacrylate (2.9 g) by extraction three times with an equal volume of aqueous sodium hydroxide (0.5 wt/v%). This sample was then mixed with an equal weight of 2-ethylhexylmethacrylate and the mixture was washed twice with water and the pH of the washings was verified as neutral to pH paper. To this mixture was added N-butyl-N'decyl-N"-(3-hydroxylpropyl)-guanidinium methacrylate (3.9 g) followed by tert-butyl perbenzoate (0.2 g). The monmers were stirred to mix fully, and then degassed by three successive freeze-pump-thaw cycles. (wt % monomers: methyl methacrylate 30 wt %, 2-ethylhexylmethacrylate 30 wt %, N-butyl-N'decylguanidinium methacrylate, 40 wt %).The degassed monomer mixture was then added dropwise over two hours to a stirred volume of refluxing xylenes (20 mL). Following addition the reflux was continued for a total reaction time of 5 hours. The cooled xylene solution of the polymer was added dropwise to vigorously stirred hexanes (150 mL), and the layers were subsequently allowed to separate. The supernatant was decanted and the process was repeated until the supernatant was clear. The residual polymer was evacuated at high vacuum to remove the solvent. A sample of this product gave an elemental analysis of 3.82 w/w % N corresponding to 28.6 w/w % N-butyl-N'decyl-N"-(3-hydroxylpropyl)-guanidinium in the product.

Test panels were prepared from a xylene solution of the polymer by evaporation onto a 10×10 cm Plexiglass panel at a total loading of 0.01 g/cm$^2$. Controls were prepared by a directly analogous method starting with tetrabuylammonium methacrylate. The field experiments were conducted simultaneously with the experiments described in Example 1 and used directly analogous analytical procedures.

The first field test in warm seawater gave barnacle settlement (28±12 barnacles settled per panel) that was significantly less than settlement on controls (86±13 barnacles settled per panel) after 22 days exposure. Slime formation from algae was also significantly reduced compared to controls after 32 days exposure (average score of controls 3.2±1; average score of treated panels 1.5±0.5). Panels prepared as previously from a urethane paint with 10 wt % of N-butyl-N'decyl-N"-(3-hydroxylpropyl)-guanidinium chloride dissolved in the matrix supported both barnacle settlement and algal growth that was statistically indistinguishable from untreated controls at both the 22 and 32 day analysis dates. Thus the biocidal activity of the N-butyl-N'decyl-N"-(3-hydroxyl propyl) guanidinium cation was prolonged by the polymer formulation.

The second field test in cool seawater gave significant inhibition of initial algal growth at 42 days (average score 1.2±0.1 on treated panels; average score 3.3±0.5 on controls), and significant reduction in barnacle settlement after 153 days exposure (average number of barnacles settled on treated panels was 10±4; average number of barnacles settled on control panels was 85±31). N-butyl-N'decyl-N"-(3-hydroxylpropyl)guanidinium chloride dispersed in a urethane paint at 10 wt % was also effective in inhibiting barnacle growth at 153 days exposure (average number of barnacles settled on treated panels was 15±9; average number of barnacles settled on control panels was 75±35) and was moderately effective in inhibiting algal growth at 32 days (average score 2.2±0.5 on treated panels; average score 3.3±0.5 on controls). Thus the biocidal activity of the N-butyl-N'decyl-N"-(3-hydroxylpropyl) guanidinium cation has been preserved by the polymer formulation.

As would be known to one skilled in the art, the foregoing is an embodiment of the invention, and variations that do not alter the scope of the invention are also contemplated. For example, the formulation of "Polymer$^-$" can be highly variable. The following parameters are preferred:

1) The anionic group should be a relatively weak base with respect to the polysubstituted guanidinium to avoid direct deprotonation which would accelerate the release of the active agent. The pK$_a$ of guanidinium cations is estimated to be approximately 12, so a pK$_a$ of less than 9 for the conjugate acid of the anionic site would be desired. This would include some phenols, hydrogenphosphates, carboxylates, and sulfonates among other possibilities.

2) The polymer component requires both mechanical and hydrolytic stability, as well acceptable processibility to form a suitable coating. Processibility is usually associated with a flexible hydrophobic segment, such as a branched alkyl ester of an acrylate. The mechanical stability is typically associated with components that increase the glass transition temperature of the polymer, such as methyl methacrylate. These competing demands indicate that a co-polymer composition is likely required. The concentrations of the active guanidinium salt within the co-polymer should be as high as possible to ensure the longest possible lifetime of the coating.

3) The proposed mechanism offers the potential for a self-polishing process to enhance the anti-fouling performance of the coating. As the ion exchange metathesis proceeds, the inherent solubility of the "Polymer$^-$" species in seawater increases. At the limit of complete exchange, an ideal copolymer formulation would be sparingly soluble so that it could dissolve and expose the underlying surface. To achieve this goal, the extent of the hydrophobic component for a polymer containing a moderately basic monoanionic exchange site such as carboxylate should not exceed about 30-40 mol % and the overall molecular weight of the fully exchanged polymer should not exceed about 100 kDa. A weaker base such as sulfonate, or a dianionic group such as phosphate could solubilize either a higher molecular weight polymer, or a more hydrophobic polymer of about the 100 kDa molecular weight range.

I claim:
1. A polymeric matrix composition comprising:
at least one structural monomer selected from esters of acrylic acid or substituted acrylic acids, amides of acrylic acid or substituted acrylic acids, styrene, substituted styrenes, acrylonitrile, substituted acrylonitriles, vinyl esters, vinyl chloride, alkenes, dienes, polyvinylic compounds, or polyalkenyl compounds; and
at least one ionic monomer comprising a salt, said salt comprising an anionic monomer that is a conjugate base of an acid having a pK$_a$ less than about 9 and at least one cationic biocide selected from

(a) guanidinium cations of general formula

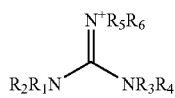

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl;
(b) quaternary ammonium cations of general formula $R_1R_2R_3R_4N^+$, where $R_1$, $R_2$, $R_3$, and $R_4$ are independently selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl; and
(c) pyridinium cations selected from N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2, 3, 4, or 5- substituted pyridinium compounds where the N substituent is selected from alkyl, branched alkyl, substituted alkyl, alkenyl, aryl or heteroaryl and where the 2, 3, 4 or 5- substituents are independently selected from alkyl, branched alkyl, substituted alkyl, alkenyl, aryl, heteroaryl, hydroxyl, O-alkyl, O-aryl, cyano, nitro, chloro, bromo, formyl, or acetyl,
wherein the at least one structural monomer and the anionic monomer are bonded to one another to form the polymeric matrix.

2. The polymeric matrix composition of claim 1 comprising about 20-70 wt % ionic monomer.

3. The polymeric matrix composition of claim 2 comprising about 20-40 wt % ionic monomer.

4. The polymeric matrix composition of claim 3 comprising about 30 wt % ionic monomer.

5. The polymeric matrix composition of claim 2 comprising at least two structural monomers.

6. The polymeric matrix composition of claim 1 wherein said cationic biocide is selected from guanidinium cations of the general formula:

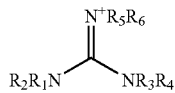

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

7. The polymeric matrix composition of claim 6 comprising about 20-70 wt % ionic monomer.

8. The polymeric matrix composition of claim 7 comprising about 20-40 wt % ionic monomer.

9. The polymeric matrix composition of claim 8 comprising about 30 wt % ionic monomer.

10. The polymeric matrix composition of claim 7 wherein said ionic monomer comprises polysubstituted guanidinium methacrylate.

11. The polymeric matrix composition of claim 10 wherein said cationic biocide is N-butyl-N'decylguanidinium, N-butyl-N'decyl-N"-(3-hydroxypropyl)guanidinium, or N-hexyl-N'-(3-hydroxypropyl)-N"-octylguanidinium.

12. The polymeric matrix composition of claim 7 wherein said structural monomers are selected from
(a) substituted alkyl, branched alkyl, or aryl esters of acrylic acid, alkyl acrylic acids, polyalkyl acrylic acids, or substituted alkyl acrylic acids;
(b) esters of alkyl acrylic acids, polyalkyl acrylic acids, or alkyl acrylic acids substituted with diols, triols, or other polyols;
(c) alkyl, substituted alkyl, branched alkyl, or aryl amides of acrylic acid, alkyl acrylic acids, polyalkyl acrylic acids, or substituted alkyl acrylic acids;
(d) amides of alkyl acrylic acids, polyalkyl acrylic acids, oralkyl acrylic acids substituted with diamines, triamines or other polyamines; or
(e) vinyl esters of alkanoic, substituted alkanoic, benzoic, or substituted benzoic acids.

13. The polymeric matrix composition of claim 12 wherein said structural monomers comprise 2-ethylhexyl acrylate and methyl methacrylate.

14. The polymeric matrix composition of claim 13 comprising greater than 0% up to 30 wt % 2-ethylhexyl acrylate and greater than 0% up to 40 wt % methyl methacrylate.

15. A polymeric matrix composition synthesized from:
at least one structural monomer selected from esters of acrylic acid or substituted acrylic acids, amides of acrylic acid or substituted acrylic acids, styrene, substituted styrenes, acrylonitrile, substituted acrylonitriles, vinyl esters, vinyl chloride, alkenes, dienes, polyvinylic compounds, or polyalkenyl compounds; and
at least one ionic monomer comprising a salt, said salt comprising an anionic monomer that is a conjugate base of an acid having a $pK_a$ less than about 9 and at least one cationic biocide selected from
(a) guanidinium cations of general formula

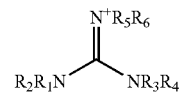

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl;
(b) quaternary ammonium cations of general formula $R_lR_2R_3R_4N^+$, where $R_1$, $R_2$, $R_3$, and $R_4$ are independently selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl; and
(c) pyridinium cations selected from N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2, 3, 4, or 5- substituted pyridinium compounds where the N substituent is selected from alkyl, branched alkyl, substituted alkyl, alkenyl, aryl or heteroaryl and where the 2, 3, 4 or 5- substituents are independently selected from the group alkyl, branched alkyl, substituted alkyl, alkenyl, aryl, heteroaryl, hydroxyl, O-alkyl, O-aryl, cyano, nitro, chloro, bromo, formyl, or acetyl, wherein the at least one structural monomer and the anionic monomer are bonded to one another to form the polymeric matrix.

16. The polymeric matrix composition of claim 15 synthesized from about 20-70 wt % ionic monomer.

17. The polymeric matrix composition of claim 16 synthesized from about 20-40 wt % ionic monomer.

18. The polymeric matrix of claim 17 synthesized from about 30 wt % ionic monomer.

19. The polymeric matrix composition of claim 16 synthesized from at least two structural monomers.

20. The polymeric matrix composition of claim 15 wherein said cationic biocide is selected from guanidinium cations of the general formula:

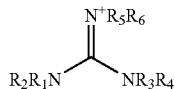

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

21. The polymeric matrix composition of claim 20 synthesized from about 20-70 wt % ionic monomer.

22. The polymeric matrix composition of claim 21 synthesized from about 20-40 wt % ionic monomer.

23. The polymeric matrix composition of claim 22 synthesized from about 30 wt % ionic monomer.

24. The polymeric matrix composition of claim 21 wherein said ionic monomer comprises polysubstituted guanidinium methacrylate.

25. The polymeric matrix composition of claim 24 wherein said cationic biocide is N-butyl-N'decylguanidinium, N-butyl-N'decyl-N''-(3-hydroxylpropyl)guanidinium or N-hexyl-N'-(3-hydroxypropyl)-N''-oetylguanidinium.

26. The polymeric matrix composition of claim 21 wherein said structural monomers are selected from
(a) substituted alkyl, branched alkyl, or aryl esters of acrylic acid, alkyl acrylic acids, polyalkyl acrylic acids, or substituted alkyl acrylic acids;
(b) esters of alkyl acrylic acids, polyalkyl acrylic acids, or alkyl acrylic acids substituted with diols, triols, or other polyols;
(c) alkyl, substituted alkyl, branched alkyl, or aryl amides of acrylic acid, alkyl acrylic acids, polyalkyl acrylic acids, or substituted alkyl acrylic acids;
(d) amides of alkyl acrylic acids, polyalkyl acrylic acids, or alkyl acrylic acids substituted with diamines, triamines or other polyamines; or
(e) vinyl esters of alkanoic, substituted alkanoic, benzoic, or substituted benzoic acids.

27. The polymeric matrix composition of claim 26 wherein said structural monomers comprise 2-ethylhexyl acrylate and methyl methacrylate.

28. The polymeric matrix composition of claim 27 synthesized from N-hexyl-N'-(3-hydroxypropyl)-N''-octylguanidinium methacrylate, methyl methacrylate and 2-ethylhexylacrylate.

29. A method, comprising treating a surface with an agent comprising a polymeric matrix, the polymeric matrix comprising:
at least one structural monomer selected from esters of acrylic acid or substituted acrylic acids, amides of acrylic acid or substituted acrylic acids, styrene, substituted styrenes, acrylonitrile, substituted acrylonitriles, vinyl esters, vinyl chloride, alkenes, dienes, polyvinylic compounds, or polyalkenyl compounds; and
at least one ionic monomer comprising a salt, said salt comprising an anionic monomer that is a conjugate base of an acid having a $pK_a$ less than about 9 and at least one cationic biocide selected from
(a) guanidinium cations of general formula

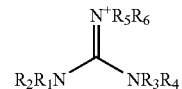

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl;
(b) quaternary ammonium cations of general formula $R_1R_2R_3R_4N^+$, where $R_1$, $R_2$, $R_3$, and $R_4$ are independently selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl; and
(c) pyridinium cations selected from N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2, 3, 4, or 5- substituted pyridinium compounds where the N substituent is selected from alkyl, branched alkyl, substituted alkyl, alkenyl, aryl or heteroaryl and where the 2, 3, 4 or 5- substituents are independently selected from alkyl, branched alkyl, substituted alkyl, alkenyl, aryl, heteroaryl, hydroxyl, O-alkyl, O-aryl, cyano, nitro, chloro, bromo, formyl, or acetyl, wherein the at least one structural monomer and the anionic monomer are bonded to one another to form the polymeric matrix.

30. The method of claim 29 wherein the polymeric matrix comprises greater than 0% up to 30 wt % 2-ethylhexyl acrylate, greater than 0% up to 40 wt % methyl methacrylate, and about 20-70 wt % of at least one ionic monomer comprising a salt, said salt comprising an anion that is a conjugate base of an acid having a $pK_a$ less than about 9 and at least one cationic biocide selected from guanidinium cations of the general formula:

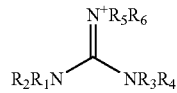

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl.

31. The method of claim 29 wherein the polymeric matrix is synthesized from 2-ethylhexyl acrylate, methyl methacrylate, and about 20-70 wt % of N-hexyl-N'-(3-hydroxypropyl)-N''-octylguanidinium methacrylate.

32. The method of claim 29 wherein treating comprises coating.

33. The method of claim 30 wherein treating comprises coating.

34. The method of claim 31 wherein treating comprises coating.

35. The polymeric matrix composition of claim 13 comprising from about 20 to about 30 wt % 2-ethylhexyl acrylate and from about 20 to about 40 wt % methyl methacrylate.

36. A composition comprising a polymeric matrix, the polymeric matrix consisting of:
at least one structural monomer selected from esters of acrylic acid or substituted acrylic acids, amides of acrylic acid or substituted acrylic acids, styrene, substituted styrenes, acrylonitrile, substituted acrylonitriles, vinyl esters, vinyl chloride, alkenes, dienes, polyvinylic compounds, or polyalkenyl compounds; and
at least one ionic monomer consisting of an anionic monomer that is a conjugate base of an acid having a $pK_a$ less than about 9 and at least one cationic biocide selected from
(a) guanidinium cations of general formula

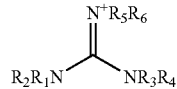

wherein $R_1$ is selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl, and $R_2$, $R_3$, $R_4$, $R_5$ and $R_6$ are independently selected from hydrogen, alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl;
(b) quaternary ammonium cations of general formula $R_1R_2R_3R_4N^+$, where $R_1$, $R_2$, $R_3$, and $R_4$ are independently selected from alkyl, substituted alkyl, cycloalkyl, substituted cycloalkyl, alkenyl, substituted alkenyl, cycloalkenyl, substituted cycloalkenyl, alkynyl, substituted aryl, heteroaryl and substituted heteroaryl; and
(c) pyridinium cations selected from N-substituted pyridinium where the N substituent is selected from alkyl, branched alkyl, substituted alkyl, alkenyl, aryl or heteroaryl; N,N'-disubstituted bipyridinium where the N and N' substituents are independently selected from alkyl, branched alkyl, substituted alkyl, alkenyl, aryl or heteroaryl; N-alkyl-2, 3, 4, or 5- substituted pyridinium compounds where the N substituent is selected from alkyl, branched alkyl, substituted alkyl, alkenyl, aryl or heteroaryl and where the 2, 3, 4 or 5- substituents are independently selected from the group alkyl, branched alkyl, substituted alkyl, alkenyl, aryl, heteroaryl, hydroxyl, O-alkyl, O-aryl, cyano, nitro, chloro, bromo, formyl, or acetyl,
wherein the at least one structural monomer and the anionic monomer are bonded to one another to form the polymeric matrix.

37. The composition of claim 36, where the cationic biocide is N-butyl-N' decylguanidinium, N-butyl-N'decyl-N''-(3-hydroxylpropyl)guanidinium, or N-hexyl-N' -(3-hydroxypropyl)-N''-octylguanidinium.

38. A polymeric matrix composition comprising:
at least one structural monomer selected from methyl methacrylate, 2-ethylhexylmethacrylate, 2-ethylhexylacrylate, or a combination thereof; and
at least one ionic monomer consisting of an anionic monomer and a cationic biocide, wherein the ionic monomer is selected from the methacrylate salt of N-butyl-N'-decylguanidinium, the methacrylate salt of N-butyl-N'-decyl-N''-(3-hydroxypropyl)guanidinium, or a combination thereof, wherein the at least one structural monomer and the anionic monomer are bonded to one another to form the polymeric matrix.

39. The polymeric matrix composition of claim 1, wherein the composition is formulated for use as a biocidal agent.

40. The polymeric matrix composition of claim 1, wherein the polymeric matrix is capable of releasing the cationic biocide via an ion-exchange reaction with another cation.

* * * * *